US005599677A

United States Patent [19]
Dowell et al.

[11] Patent Number: 5,599,677
[45] Date of Patent: Feb. 4, 1997

[54] IMMUNOASSAYS FOR PROSTATE SPECIFIC ANTIGEN

[75] Inventors: Barry L. Dowell, Mundelein; Carol A. King, Highland Park; Debra B. Alexander, Gurnee; Allan H. Smith, Zion; Susan B. O'Morchoe, Woodridge, all of Ill.

[73] Assignee: Abbott Laboratories, Abbott Park, Ill.

[21] Appl. No.: 174,964

[22] Filed: Dec. 29, 1993

[51] Int. Cl.$^6$ ...................... G01N 33/543; G01N 33/573; G01N 33/574; G01N 33/577

[52] U.S. Cl. .................... 435/7.4; 435/7.23; 435/7.94; 435/962; 436/518; 436/548; 436/813

[58] Field of Search ..................... 435/7.23, 7.4, 435/7.94, 962; 436/518, 548, 813

[56] References Cited

U.S. PATENT DOCUMENTS

| | | | |
|---|---|---|---|
| 4,737,456 | 4/1988 | Weng et al. | 435/7 |
| 4,849,353 | 7/1989 | Harpel | 435/7.4 |
| 5,026,653 | 6/1991 | Lee et al. | 436/518 |
| 5,114,863 | 5/1992 | McCombs et al. | 436/518 |
| 5,324,634 | 6/1994 | Zucker | 435/7.23 |

FOREIGN PATENT DOCUMENTS

| | | |
|---|---|---|
| 0241444 | 10/1987 | European Pat. Off. . |
| 0288793 | 11/1988 | European Pat. Off. . |
| WO9201936 | 2/1992 | WIPO . |

OTHER PUBLICATIONS

"Immunoaffinity Chromatography with Affinity Supports", *Bio–Rad Bulletin 1099*, (1990).

H. Lilja et al., "Prostate Specific Antigen Predominantly Forms a Complex with Alpha$_1$–Antichymotrypsin in Blood", *Cancer Supplement*, 70 (1992), pp. 230–234.

K. Pettersson et al, "Development of Immunoflourometric Methods for PSA to Improve the Discrimination Between Early Prostate Cancer and Benign Prostatic Hyperplasia" *XV International Congress of Clinical Chemistry* (1993).

O. Nilsson et al., "Epitope mapping of PSA, and development of asays for the determination of different isoforms of PSA", *CanAg Diagnostics AB*, (1993).

"Epitope mapping of PSA, and development of asays for the determination of different isoforms of PSA", Abstract P38, *Journal Tumor Marker Oncology*, (1993) 10th Int'l Conference on Human Tumor Markers.

Pharmacia LKB Biotechnology, *Affinity Chromatography principles & methods*.

W. G. Wood et al., "The Establishment and Evaluation of Luminescent–Labelled Immunometric Assays for Prostate–Specific Antigen–$\alpha_1$-Antichymotrypsin Complexes in Serum", *European Journal Clinical Chemistry Clinical Biochemistry*, 29(1991), pp. 787–794.

Pharmacia LKB Biotechnology, "Coupling gels for ligand immobilization", Affinity Chromatography principales & methods, (1993) pp. 23–30.

A. Christensson et al., "Serum Prostate Specific Antigen Complexed to $\alpha$1–Antichymotrypsin as an indicator or Prostate Cancer", *Journal of Urology*, 150(1993), pp. 100–105.

U. Stenman et al., "A Complex between Prostate–specific Antigen and $\alpha$1–Antichymotrypsin Is the Major Form of Prostate–specific Antigen in Serium of Patients with Prostatic Cancer: Assay of the Complex Improves Clinical Sensitivity for Cancer" *Cancer Research*, 51(1991) pp. 222–226.

H. Lilja et al., "Prostate–Specific Antigen in Serum Occurs Predominantly in Complex with $\alpha$1–Antichymotrypsin", *Clinical Chemistry*, 37,(1991) pp. 1618–1625.

B. Bluestein et al., "Multi–Site Clinical Evaluation of an Automated Chemiluminescent Immunoassay for Prostate Specific Antigen (ACS™PSA)", *Journal of Tumor Marker Oncology*, 7(1992), pp. 41–60.

K. Watt et al., "Human prostate–specific antigen: Structural and functional similarity with serine proteases", *Proc. Natl. Acad. Sci. USA*, 83(1986), pp. 3166–3170.

Y. Ban et al., "The Proteolytic Activity of Human Prostate–Specific Antigen", *Biochemical and Biophysical Research Communications*, 123 (1984), pp. 482–490.

T. A. Stamey et al., "Prostate–Specific Antigen as a Serum Marker for Adenocarcinoma of the Prostate", *The New England Journal of Medicine*, 317 (1987), pp. 909–916.

M. Kurlyama et al., "Multiple Marker Evaluation in Human Prostate Cancer with the use of Tissue–specific Antigens", *J. Nat'l Cancer Inst.*, 68 (1982), pp. 99–105.

P. H. Lange et al., "Serum Prostate–Specific Antigen: its use in Diagnosis and Management of Prostate Cancer" *Supplement to Urology*, 33 (Jun. 1989) pp. 13–17.

M. K. Brawer et al., "Prostate–Specific Antigen in Management of Prostatic Carcinoma", *Supplement to Urology*, 33(May 1989) pp. 11–16.

P. H. Lange et al., "The Value of Serum Prostate Specific Antigen Determinations Before and After Radical Prostatectomy", *Journal of Urology*, 141(1989), pp. 873–879.

T. A. Stamey et al., "Prostate Specific Antigen in the Diagnosis and Treatment of Adenocarcinoma of the Prostate.II. Radical Prostatectomy Treated Patients", *The Journal of Urology*, 141 (1989), pp. 1076–1083.

J. E. Oesterling et al., "Prostate Specific Antigen in the Preoperative and Postoperative Evaluation of Localized Prostatic Cancer Treated with Radical Prostatectomy", *The Journal of Urology*, 139(1988), pp. 766–772.

(List continued on next page.)

Primary Examiner—David Saunders
Attorney, Agent, or Firm—Lawrence S. Pope

[57] ABSTRACT

The present invention relates to the field of cancer immunoassay. Specifically, a new immunoassay method for prostate specific antigen (PSA) is presented. Also presented is a complex which resembles a complex of PSA and $\alpha$-antichymotrypsin (ACT) that can be used as a calibrator or control in an immunoassay for PSA. Further presented is a method for fractionating polyclonal antibodies, to PSA, into those which bind epitopes that are masked by the binding of PSA to ACT and those which do not bind such epitopes.

33 Claims, 3 Drawing Sheets

OTHER PUBLICATIONS

W. H. Scouten, "Affinity Chromatography for protein isolation", *Current Opinion in Biotechnology*, 2 (1991), pp. 37–43.

M. Flore, "The Abbott IMx™ Automated Benchtop Immunochemistry Analyzer System", *Clinical Chemistry*, 34 (1988), pp. 1726–1732.

M. J. Duffy, "New cancer Markers", *Ann Clin Biochem*, 26 (1989), pp. 379–387.

A. Lundwall, "Characterization of the gene for Prostate–specific antigen, a human glandular kallikrein", *Biochemical and Biophysical Research Communicatications*, 161(1989), pp. 1151–1159.

M. Kuriyama, "Quantitation of Prostate–specific Antigen in Serum by a Sensitive Enzyme Immunoassay", *Cancer Research*, 40 (1980) pp. 4658–4662.

D. W. Chan, "Prostate–Specific Antigen as a Marker for Prostatic Cancer: a Monoclonal and a Polyclonal Immunoassay Compared", *Clinical Chemistry*, 33 (1987) pp. 1916–1920.

C. S. Killian, "Prognostic Importance of Prostate–specific Antigen for Monitoring Patients with States $B_2$ to $D_1$ Prostate Cancer", *Cancer Research*, 45(1985) pp. 886–891.

C. Schneider, "A One–step Purification of Membrane Proteins Using a High Efficiency Immunomatrix", *The Journal of Biological Chemistry*, 257(1982), pp. 10766–10769.

A. Johnstone, "Affinity chromatography and immunoprecipitation", *Immunochemistry in Practice*, Scientific Publications, Oxford, 1st Edition (1982) pp. 202–232.

T. H. Ji, "Bifunctional Reagents", *Methods in Enzymology*, 91(1983), p. 580.

SS. Wong, "Protein Chemical Cross–Linking", *Biocatalyst Design for Stability and Specificity*, Chp. 22, pp. 266–282.

A. Barnes, "The Abbott IMx® and IMx Select™ Systems", *Journal Clin. Immunoasssay, 2 (1991), pp. 115–119*.

M. C. Wang, "Purification of a Human Prostate Specific Antigen", *Investigative Urology 17, pp. 159–163*.

J. K. Siddall, "An Evaluation of the Immunochemical Measurement of Prostatic Acid Phosphatase and Prostatic Specific Antigen in Carcinoma of the Prostate", *Euro, Urol.*, 12(1986), pp. 123–130.

T. A. Stamey, "Prostate Specific Antigen in the Diagnosis and Treatment of Adenocarcinoma of the Prostate. IV. Anti––Androgen Treated Patients", *The Journal of Urology*, 141(1989), pp. 1088–1090.

T. A. Stamey, "Prostate Specific Antigen in the Diagnosis and Treatment of Adenocarcinoma of the Prostate. III. Radiation Treated Patients", *The Journal of Urology, '141(1989), pp. 1084–1087*.

R. L. Lundblad, *Chemical Reagents for Protein Modification*, 2nd Edition, CRC Press, 1991.

M. N. Gupta, "Cross–Linking Techniques", *Biocatalyst Design for Stability and Specificity, pp. 308–326*.

M. M. Manson, ed., "Immunochemical Protocols" *Methods in Molecular Biology*, 10(1992), pp. 89–91.

PART A
STEP A1

STEP A2

PART B
STEP B1

FREE PSA

STEP B2

FREE PSA       PSA-ACT COMPLEX

STEP B3

FREE PSA       PSA-ACT COMPLEX

PART A

PART B

PART C

IMMUNOASSAYS FOR PROSTATE SPECIFIC ANTIGEN

FIELD OF THE INVENTION

The present invention relates to the field of cancer immunoassay. Specifically, a new immunoassay method for prostate specific antigen (PSA) is presented. Also presented is a PSA-anti-PSA complex which resembles a complex of PSA and $\alpha_1$-antichymotrypsin (ACT) that can be used as a calibrator and/or Control in an immunoassay for PSA. Further presented is a method for fractionating anti-PSA polyclonal antibodies, into those which bind epitopes that are masked by the binding of PSA to ACT and those which do not bind such epitopes.

BACKGROUND OF THE INVENTION

Prostate specific antigen (PSA) was first described by Wang, M. C., et al., *Invest Urol*, 17:159 (1979). It is a secretion of prostate epithelium and is also produced by prostate cancer cells. PSA was characterized as a glycoprotein monomer of 33–34,000 dalton molecular weight with protease activity (Wang, M. C., et al., supra and Ban, Y, et al., *Biochem Biophys Res Commun.* 123:482 (1984)). More recently the amino acid sequence of the antigen has been reported (Watt, W. K., et al., *Proc Natl Acad Sci USA*, 83:3166 (1986)) and the gene for PSA has been cloned (Lundwall, A., *Biochem Biophys Res Commun.* 161:1151 (1989)). Development of an enzyme immunoassay by Kuriyama, et al, made it possible to detect low concentrations of PSA in the blood of patients with malignant and benign prostate disease and a significant proportion of normal males (Kuriyama, M. et al., *Cancer Res.* 40:4658 (1980)).

PSA testing can have significant value in detecting metastatic or persistent disease in patients following surgical or medical treatment of prostate cancer (Lange, P. H., et al., *Urology* 33(6 Suppl): 13, (June, 1989); and Killian, C. S., et al., *Cancer Res* 45:886 (1985)). Persistent elevation of PSA following treatment or an increase in the post-treatment baseline PSA level is indicative of recurrent or residual disease (Brawer, M. K., et al., *Urology*, 33 (5 Suppl): 11 (May, 1989); Siddal, J. K., et al., *Eur Urol* 12:1:3 (1986); Stamey, T. A., et al., *N Engl J Med* 317:909 (1987); Lange, P. H. et al., *J Urol.* 141:873 (1989); Stamey, T. A., et al., *J Urol.* 141:1076 (1989); Stamey, T. A., et al., *J Urol* 141:1084, (1989); Stamey, T. A., et al., *J Urol* 141:1088 (1989); and Chan, D. W., et al., *Clin Chem* 33:1916 (1987)).

PSA testing alone is not recommended as a screening procedure in the general population nor as a guide in disease staging. Instead, it is widely accepted as an adjunctive test in the management of prostate cancer patients (Kuriyama, M. et al., *J Natl Cancer Inst* 68:99 (1982 ); Stamey, T. A., et al., *N Engl J Med* 317:909 (1987); Lange, P. H. et al., *J Urol.* 141:873 (1989); Stamey, T. A., et al., *J Urol.* 141:1076 (1989); Stamey, T. A., et al., *J Urol* 141:1084 (1989); Stamey, T. A., et al., *J Urol* 141:1088 (1989); Chan, D. W., et al., *Clin Chem* 33:1916 (1987); and Oesterling, J. E., et al., *J Urol.* 139:766 (1988)).

Measurements of the serum concentration of PSA have now found widespread use in monitoring of patients with prostate cancer, although increased serum concentrations of PSA have also been reported in benign prostatic hyperplasia and secondary to surgical trauma of the prostate (Duffy, *Ann Clin Biochem*, (1989); Brawer, et al., *Urology Suppl*, (1989)).

PCT patent application WO 92/01936, "Assay of Free and Complexed Prostate Specific-Antigen (PSA)" to Lilja, H. et al., published Feb. 6, 1992, discloses immunoassays for free PSA as well as PSA as a proteinase inhibitor complex. The free PSA and the PSA complex are measured by a non-competitive immunoassay employing at least two different monoclonal antibodies. The invention is further characterized in that the PSA proteinase inhibitor complex of interest is formed either with $\alpha_1$-antichymotrypsin (ACT), $\alpha_1$-protease inhibitor (API) or $\alpha_2$-macroglobulin. Moreover, the invention is characterized in that free PSA, the PSA-proteinase inhibitor complex and their ratio to total PSA are applied in the diagnosis of patients with prostate cancer.

The patent application discloses three monoclonal antibodies ("MAB"). PSA complexed to ACT ("PSA-ACT complex") and free PSA were identified by MAB 2E9 and 2H11. MAB 5A 10 recognizes free PSA but not PSA-ACT complex. MAB 2E9 is the only anti-PSA MAB that readily identified free PSA and PSA-ACT complex on immunoblots. None of the anti-PSA MAB 2E9, 2H11 or the 5A10 significantly blocked the binding of each other to solid phase-bound PSA.

By using different combinations of the MAB in non-competitive immunoassays of human sera, the application found that increased clinical specificity is achieved by measuring both free PSA and PSA-ACT complex and that the ratios between free PSA/total PSA and free PSA/PSA-ACT complex are significantly different between benign prostatic hyperplasia and prostate cancer patients.

MAB specific for free PSA and those reactive with PSA-ACT complex are commercially available, for example, from CanAg Diagnostics AB, Gothenburg, Sweden. Through inhibition studies and analyses of dose-response of different combinations of their MAB, CanAg Diagnostics AB found at least 9 major antigenic determinant groups on the PSA molecule. One group of its MAB-defined epitopes was exposed both on uncomplexed PSA and PSA-ACT complex, and another group of its MAB-defined epitopes was exposed only in free PSA. (CanAg Diagnostics AB, Nilsson et al., *Epitope mapping of PSA, and development of assays for determination of different isoforms of PSA, and the abstract of the same title*, Abstract P 38, *J. Tumor Marker Oncology*, 10th Int'l Conference on Human Tumor Markers, Sep. 8–11, 1993, Bonn, Germany).

Competitive radioimmunoassays for PSA are commercially available (e.g., from PROS-CHECK PSA, Yang Laboratories, Inc., Bellevue, Wash.). PROS-CHECK PSA uses polyclonal rabbit antibodies to PSA, and PSA labelled with Iodine$^{125}$.

Currently, there are two types of PSA non-competitive sandwich immunoassays on the market. The first type are sandwich assays which use two sets of MAB specific for PSA: (1) one set of MAB ("capture antibodies") is bound onto a solid phase to capture PSA in a sample, and (2) the other set of MAB ("probe antibodies") is labelled and in free solution to bind the captured PSA for its detection. These assays are herein referred to as "MONO assays". Generally, the binding of these MAB to PSA is not prevented by the binding of ACT to PSA. That is, generally, these MAB can bind both free PSA and the PSA-ACT complex. Examples of such assays are the Hybritech Tandem-E and Tandem-R PSA Assays (Hybritech, La Jolla, Calif.).

The second type of sandwich assays uses MAB specific for PSA on the solid phase, and polyclonal antibodies to PSA as probe antibodies. Generally, in these assays, the MAB can bind both free PSA and the PSA-ACT complex. In contrast, the pool of polyclonal antibodies contains antibodies which can bind both free PSA and the PSA-ACT complex, and antibodies which can bind free PSA but not the PSA-ACT complex. In the latter case, the epitopes bound by these antibodies are blocked by the binding of the ACT to PSA. Examples of these assays are the Abbott IMx® PSA Assay (Abbott Laboratories, Abbott Park, Ill.), and the ACS™ PSA Assay (Ciba-Corning Diagnostics Corporation, East Walpole, Mass.).

It has been found that the second type of sandwich assays preferentially detects free PSA over that of PSA-ACT complex (this phenomenon is herein referred to as "bias"). On the other hand, some MONO assays do not exhibit such a bias. See Bluestein, B., et al., *J. Tumor Marker Oncology*, 7(4) 41 (1992).

It has been found that in the serum of patients with benign prostatic hyperplasia (BPH), there are more free PSA than PSA-ACT complexes. On the other hand, in the serum of prostate cancer patients, there are more PSA-ACT complexes than free PSA. (Lilja, H., et al., *Clin. Chem.*, 37:1618 (1991); Stenman, U., et al., *Cancer Res.*, 51:222 ( 1991 ); Lilja, H., et al., *Cancer Suppl.*, 70:230 (1992); Christensson, A., et al., *J. Urology*, 150: 100 (1993)).

SUMMARY OF THE INVENTION

One aspect of the invention presents new MOLY and MONO assays for detecting and quantitating PSA in a sample, wherein the sample is treated with $HE_{PSA}$ Antibodies which bind free PSA but not a complex of PSA and ACT ("PSA-ACT complex"). The addition of $HE_{PSA}$ Antibodies to the assays reduces or eliminates bias in these assays. Also presented are kits for conducting these assays.

Another aspect of the invention presents a complex of PSA and $HE_{PSA}$ Antibodies ("PSA-$HE_{PSA}$ Antibodies complex"), which resembles PSA-ACT complex. This complex is useful as a calibrator and/or control for PSA immunoassays.

Another aspect of the invention presents a method for fractionating polyclonal antibodies to PSA to obtain fractions containing antibodies which bind epitopes that are masked ("hidden epitopes") by the binding of PSA to ACT and those which do not bind such epitopes. Also presented are affinity columns useful for such fractionations.

The above aspects of the invention can be applied generally to any analyte which can exist in a free state or complexed to a binding molecule.

DETAILED DESCRIPTION OF THE INVENTION

Figure 1A:
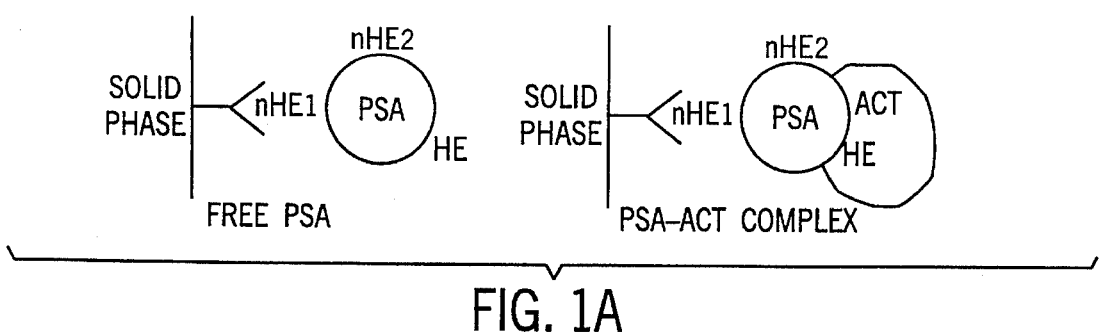
FIG. 1A is an illustration of a Step A1 in the conventional method of assaying for PSA, showing how free PSA and PSA-ACT complex result in differing relative responses.

As used herein, the term "antibodies" includes both polyclonal and monoclonal antibodies, whole immunoglobulins and antigen binding fragments of the immunoglobulins. Examples of these fragments are Fab, F(ab')$_2$ and Fv. Such fragments can be produced by methods known in the art.

As used herein, the term "HE Antibodies" or "αHE" denotes antibodies whose binding to their target antigen ("Analyte") would be prevented by the binding of another molecule ("Binding Molecule") to the Analyte. The term "Non-HE Antibodies" or "αHE" denotes antibodies whose binding to the Analyte is not prevented by the binding of the Binding Molecule to the Analyte. The epitope on the Analyte which is masked by the binding of the Binding Molecule to the Analyte is termed "hidden epitope" ("HE"). Similarly, the epitope on the Analyte which is not masked by the binding of the Binding Molecule to the Analyte is termed "non-hidden epitope" ("nHE"). The term "αAnalyte" or "αA" denotes any antibody Which is directed to the Analyte, whether it is an αHE or αnHE.

Analyte is preferably an antigen found in a biological sample, and is preferably endogenous to the sample. The Binding Molecule is preferably endogenous to the sample and is often associated with the Analyte. Preferably, the Binding Molecule and the Analyte are proteins. Examples of Analytes are serum proteases and their Binding Molecules are serum protease inhibitors. Some of the serum proteases and their inhibitors (in parentheses) are: protein C (protein C inhibitor); elastase (anti-trypsin); cathepsin G (ACT); PSA (ACT); PSA ($α_2$-macroglobulin); thrombin (anti-thrombin III); $C_1$-esterase ($C_1$-inhibitor); t-PA (PAl-1); uPA (PAl-1); plasmin ($α_2$-antiplasmin); PSA ($α_1$-protease inhibitor); and PSA (protein C inhibitor). "PAl-1" denotes plasminogen activator inhibitor Type 1. "t-PA" denotes tissue plasminogen activator. "uPA" denotes urinary plasminogen activator. One skilled in the art would realize that the Binding Molecule can be serum proteases and the Analyte can be serum protease inhibitors.

The term "MOLY assay" describes an immunoassay in which the capture antibodies are MAB and the probe antibodies are polyclonal antibodies, or vice versa.

The present invention discloses an immunoassay for an Analyte in a test sample. The sample is generally a biological sample. The biological sample can be biological fluids such as blood, serum, plasma, prostatic fluid, seminal fluid, urine, lymph and spinal fluid.

If a sample contains Analytes which are not bound to the Binding Molecule (these unbound Analytes are herein also referred to as "free Analytes") and Analytes which are complexed to the Binding Molecules ("complexed Analytes" or "Analyte-Binding Molecule complexes"), a MOLY assay and some MONO assays for the Analytes would exhibit a bias in that a sample without complexed Analytes will have a higher reading than a sample with complexed Analyte. This can occur if, e.g., some members of the polyclonal antibodies used to detect the Analyte can bind free Analyte but not complexed Analyte.

The present invention discovers that the bias found in MOLY and some MONO assays for Analytes can be corrected by adding free HE Antibodies into the reaction mixture. Other than the addition of the free HE Antibodies, the MOLY and MONO assays for a particular Analyte can be conducted according to methods known in the art for such assays. Additionally, if the Analyte in a sample is capable of being directly bound to a solid phase when the sample is incubated with the solid phase, then a capture antibody is not necessary. Probe and capture antibodies can be produced according to methods known in the art. The probe antibodies can be labelled according to methods known in the art with labels such as chemilumiscent, fluorescent, enzyme and radioactive labels, and the assays accordingly tailored to the labels involved. An example of luminescent-labelled immunometric assays is Wood, W. G., et al., *Eur. J. Clin. Chem. Clin. Biochem.*, 29: 787 (1991). The HE and Non-HE Antibodies can be produced using methods known, such as those used for producing $HE_{PSA}$ and Non-$HE_{PSA}$ Antibodies discussed below. The HE Antibodies are preferably monoclonal antibodies or specific polyclonal HE Antibodies as described below.

One aspect of this invention thus presents a sandwich noncompetitive immunoassay for an Analyte in a biological sample. A capture antibody ("αnHE") which is directed to a non-hidden epitope of the Analyte is attached to a solid phase to capture any Analyte that may be present in the biological sample. The capture antibody is incubated with HE Antibodies ("αHE") simultaneously with or after the addition of the biological sample. Alternatively, αHE may also be incubated with the sample before it is exposed to the capture antibody. Preferably, the αHE is a MAB. The incubation lasts for a sufficient time to allow the complex of {(αnHE)(Analyte)(αHE)} to form. Next, any reagents that are not bound to the solid phase are removed from the reaction mixture. This can be done by a washing step known to those skilled in the art. For example, the unbound reagents are dissolved in an aqueous medium and washed away from the solid phase, leaving the complex of {(αnHE)(Analyte)(αHE)} on the solid phase.

Next, polyclonal anti-Analyte antibodies ("αAnalyte*") are added. αAnalyte* are preferably labeled for detection, e.g. with enzyme, radioactive, fluorescent, or chemiluminiscent labels.

The reaction mixture is incubated for a sufficient time for the formation of {(αnHE)(Analyte)(αHE)(αAnalyte*)} complex and {(αnHE)(Analyte)(Binding Molecule)(αAnalyte*)} complex. Note that in the complex of {(αnHE)(Analyte)(αHE)(αAnalyte*)}, both αHE and αAnalyte* are bound to the Analyte in the complex. Note that if a Binding Molecule is present in the sample, another complex may also be formed, i.e. the complex of {(αnHE)(Analyte)(Binding Molecule)(αAnalyte*)}.

Next, the unbound reagents are separated. The formations of the complexes of {(αnHE)(Analyte)(αHE)(αAnalyte*)} and {(αnHE)(Analyte)(Binding Molecule)(αAnalyte*)} on the solid phase are detected by detecting the labeled αAnalyte*. If Analyte is not present in the sample, these complexes will not be present. The presence of these complexes is directly proportional to the Analyte concentration in the sample. Alternatively, one can assay for the presence of the remaining unbound labelled αAnalyte*, the amount of which is inversely proportional to the presence of the Analyte in the sample.

The above assay format can also be used in MONO assays which exhibit bias. In a MONO assay, the above discussion will apply, except that the αAnalyte* is labelled αnHE (i.e. "αnHE*").

In the case where the capture antibody is a polyclonal antibody and the probe antibody is a MAB, the above discussion will apply except that the capture antibody is αAnalyte or αnHE (αnHE can be fractionated from polyclonal antibodies, e.g. by the fractionation methods described below), and the probe antibody is αnHE*. If the capture antibodies, αAnalyte, contain a subpopulation of αHE, there will also be an additional complex of {(αHE)(Analyte)(αnHE*)} resulting from the above assay steps.

The above discussion presumes that there is only one HE on the Analyte. However, it shall be noted that if a particular αHE does not mask all the HE on the Analyte, then additional HE Antibodies directed to other HE sites on the Analyte are to be used.

One skilled in the art would realize that a probe antibody need not be labeled if it can be specifically bound by another molecule which is labeled. Further, if the Analyte can be directly bound to the solid phase, then a capture antibody need not be used.

Also presented in this application are assay kits for conducting the above assays. Preferably, the assay kit has a container containing unlabelled HE Antibodies; and another container containing capture antibodies directed to the Analyte, preferably these antibodies are directed to non-HE, more preferably they are MAB, most preferably, they are bound to a solid phase. The unlabelled HE Antibodies can be in a separate container or in the same container as the capture antibodies or the probe antibodies. For a MOLY Assay, the kit may additionally have: a container containing probe polyclonal antibodies to Analyte and preferably the antibodies are labeled for detection; and another container containing reagents which would react with the labels on the antibodies to emit a signal. For example, the polyclonal antibodies can be labeled with an enzyme such as alkaline phosphatase and the reagent which would react with it will be the enzyme substrate. In the case of alkaline phosphatase, 4-methylumbelliferyl phosphate (MUP) has been found to be convenient and the reaction is described in Example II below. Alternatively, the probe antibodies can be monoclonal antibodies, and the capture antibodies can be polyclonal antibodies. In such a case, the monoclonal probe antibodies are preferably Non-HE Antibodies. For a MONO assay, the probe and capture antibodies are MAB directed to the Analyte. Preferably, the probe and capture MAB are non-HE Antibodies. In the above kits, the antibodies are preferably in a solution, such as a buffer, which has no adverse effect on immunoassay. The above kits may additionally have container(s) containing calibrator(s) and/or container(s) containing control(s). For an Analyte Assay, the preferred calibrator and control contain free Analyte, the complex of Analyte-HE Antibodies, or the complex of Analyte-Binding Molecule described below.

In the preferred invention, the Analyte is PSA, and the Binding Molecule is ACT. The HE Antibodies to PSA are those which bind free PSA but not PSA-ACT complex.

These antibodies are herein also referred to as "HE$_{PSA}$ Antibodies". The corresponding Non-HE Antibodies are also referred to as "Non-HE$_{PSA}$ Antibodies".

The methods for obtaining HE$_{PSA}$ Antibodies (and Non-HE$_{PSA}$ Antibodies) are known in the art. For example, they are described in PCT patent application WO 92/01936, to H. Lilja et al., supra, and CanAg Diagnostics AB, Nilsson et al., *Epitope mapping of PSA, and development of assays for determination of different isoforms of PSA* (1993) and its Abstract of the same title, supra,. Examples of HE$_{PSA}$ Antibodies are: (1) MAB 5A 10 as described in WO 92/01936; (2) MAB 9B10 which is disclosed in K. Pettersson et al., *Development of Immunofluorometric Methods for PSA to Improve the Discrimination Between Early Prostate Cancer and Benign Prostatic Hyperplasia*. XV International Congress of Clinical Chemistry, Melbourne, Australia, Nov. 14–19 (1993) which also discloses MAB H117 and H50; and (3) MAB PSA6, PSA30, PSA17, PSA19, PSA20, and PSA25 which are commcercially available from CanAg Diagnostics AB, Gothenburg, Sweden. U.S. patent application Ser. No. 08/094,901, filed on Jul. 22, 1993 and now abandoned, to Matikainen, M., et al. discloses both MAB 5A10 and 9B10, their production and characteristics; the hybridomas secreting these MABs are therein designated 5A10E7F11H4 and 9B10A9H3, respectively. These hybridomas were deposited with the European Collection of Animal Cell Cultures (ECACC), Public Health Laboratory Service, Centre for Applied Microbiology and Research, Porton Down, Salisbury, Wiltshire SP40JG, Great Britain on Mar. 12, 1993, and given ECACC accession Nos. 93031201 and 93031202, respectively. The above publications and applications are hereby incorporated by reference.

Thus, in particular, the present invention presents three inventions useful for PSA assays: new PSA assays using HE$_{PSA}$ Antibodies; a method for selecting specific polyclonal HE$_{PSA}$ Antibodies and antibodies for non-hidden epitopes; and PSA-HE$_{PSA}$ Antibody complex which resembles PSA-ACT complex. The first two inventions avoid or reduce bias present in the prior art MOLY assays. The last invention is useful as calibrator and/or control for both the MONO and MOLY PSA assays. The specific polyclonal Non-HE$_{PSA}$ Antibodies selected by the second method can also be used in both MOLY (as either probe or capture antibodies, or both) and competitve (as capture antibodies) immunoassays for PSA. On the other hand, HE$_{PSA}$ Antibodies could be used in assays specific for free PSA or they could be used in PSA immunoassays (whether MOLY or MONO) suffering from a bias to alleviate or eliminate such bias, as described above.

The present application uses PSA, ACT, and HE$_{PSA}$ Antibodies and Non-HE$_{PSA}$ Antibodies to illustrate the invention. However, one skilled in the art would understand that the invention can be applied to any Analyte, Binding Molecule, and HE Antibodies and Non-HE Antibodies, respectively.

I. NEW PSA IMMUNOASSAY METHOD

Figure 1B:
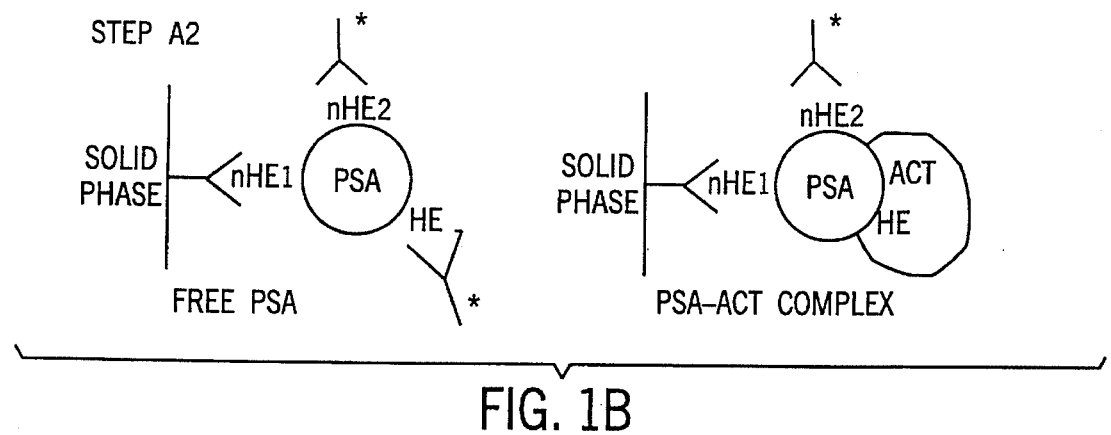
FIG. 1B is an illustration of a Step A2 in the conventional method of assaying for PSA, showing how free PSA and PSA-ACT complex result in differing relative responses.
Figure 2A:
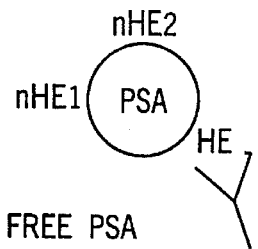
FIG. 2A is an illustration of a Step B1 in the method according to the invention of assaying for PSA, showing how $HE_{PSA}$ antibodies modify assay specificity for free PSA and PSA-ACT complex.
Figure 2A:
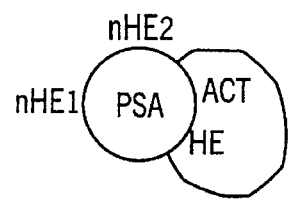
Figure 2B:
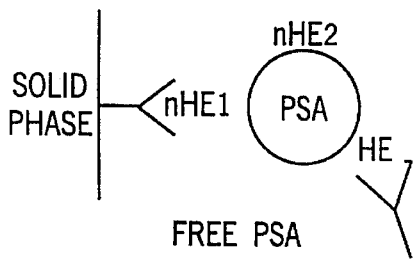
FIG. 2B is an illustration of a Step B2 in the method according to the invention of assaying for PSA, showing how $HE_{PSA}$ antibodies modify assay specificity for free PSA and PSA-ACT complex.
Figure 2B:
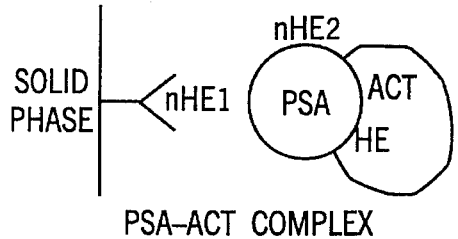
Figure 2C:
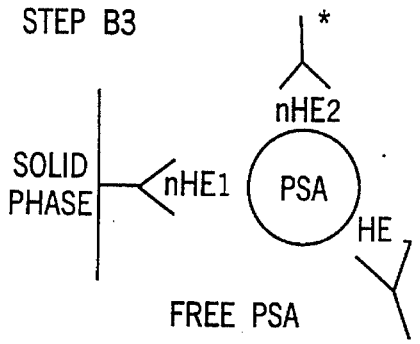
FIG. 2C is an illustration of a Step B3 in the method according to the invention of assaying for PSA, showing how $HE_{PSA}$ antibodies modify assay specificity for free PSA and PSA-ACT complex.
Figure 2C:
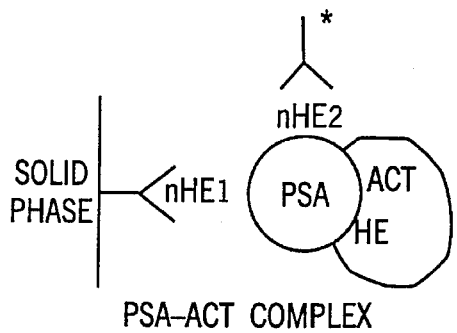

FIG. 1A and 1B compares the conventional PSA MOLY assay (Part A) and the PSA MOLY assay of the present invention in FIG. 2A, 2B, and 2C (Part B) to illustrate how HE$_{PSA}$ Antibodies modify assay specificity for free PSA and PSA-ACT complex.

Part A presents the conventional MOLY assay which suffers from bias. The procedural steps in Part A are the same as Part B except that P:art B has the additional step of Step B1.

The steps in Part A are as follow:

Step A1

Capture with non-HE Antibodies to Epitope 1 (αnHE1). A Non-HE Antibody (αnHE1) which is specific for a non-hidden epitope (designated nHE1) on the PSA molecule is linked to a solid phase. When a sample containing either free PSA or PSA-ACT complex is allowed to react with the solid phase bound αnHE1, both free PSA and PSA-ACT complex can bind exclusively through the nHE1 epitope. The HE site is masked by binding of ACT. On the other hand, the HE is still available on free PSA for subsequent reaction with other antibodies.

Step A2

Reaction with Polyclonal Conjugate Containing Antibodies to Non-Hidden Epitope 2 (αnHE2) and to Hidden Epitope (αHE*). The subsequent addition of labelled polyclonal antibodies to PSA ("labelled polyclonals"), which contain both labelled antibodies specific for HE (αHE*) and antibodies specific for non-HE2 (αnHE2*), will result in the binding of both types of antibodies to the free PSA. In contrast, since HE is masked by ACT in the PSA-ACT complex, the same labelled polyclonals can only bind to the non-hidden epitope nHE2. These labelled polyclonals are conjugated to a label for detection purpose. Examples of labels are: chemiluminiscent labels, radioactive labels, and enzyme labels which are known in the art. In this example, the label is an enzyme. The unbound reagents are removed from the solid phase, e.g., by Washing the solid phase using methods known in the art.

Step A3

Then the enzyme substrate is added to the solid phase and the enzymatic product generates a signal which is monitored. The free PSA which has bound two labelled polyclonals generates twice the signal as the PSA-ACT complex, which has bound only one labelled polyclonal resulting in a positive bias for the free form of PSA.

Part B in FIGS. 2A, 2B and 2C presents the assay of the present invention in which unlabelled HE$_{PSA}$ Antibodies are added (in Step B1) to the assay described in Part A and this results in an assay without bias.

The steps in Part B are as follow:

Step B1

Pretreatment of Sample with Unlabeled Antibodies to Hidden Epitopes (αHE). The sample is pretreated with an unlabelled HE$_{PSA}$ Antibody (αHE). This antibody reacts with HE on the free PSA, but it does not bind to PSA-ACT complex. The HE site is masked by binding of ACT. Alternatively, the unlabelled αHE can be added in Step B2 or Step B3, respectively.

Step B2

Capture with non-HE Antibodies to Epitope 1 (αHE1). The sample is added to solid phase bound αnHE1 antibody as in Part A.

Step B3

Reaction with Polyclonal Conjugate Containing Antibodies to Non-Hidden Epitope 2 (αnHE2*) and to Hidden Epitope (αHE*). The subsequent addition of labelled polyclonals containing labelled antibodies which recognize HE (αHE*) and antibodies which recognize non-HE (αnHE2*) will result in the binding of αnHE2* to both free PSA and PSA-ACT complex. αHE* cannot bind free PSA nor PSA-ACT complex, because HE is masked by unlabelled αHE in the free PSA and by ACT in the PSA-ACT complex.

Step B4

The substrate is added and the signal monitored. Both free PSA and PSA-ACT complex generate equivalent signal, because both have only bound the αnHE2*. This results in an assay without bias to free PSA compared to the PSA-ACT complex.

Materials for the solid phase can be any of those used for immunoassays. Natural, synthetic or naturally occurring materials that are synthetically modified can be used. They include: polysaccharides, e.g., cellulose materials including paper, cellulose and cellulose derivatives such as cellulose acetate and nitrocellulose; silica; fiberglass; inorganic materials such as deactivated aluminium, diatomaceous earth or other inorganic finely divided material uniformly dispersed in a porous polymer matrix made of polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; agarose; Sephadex (Pharmacia Fine Chemicals, Inc., Piscataway, N.J.); Trisacryl (Pointet-Girard, France); sillicon particles; porous fibrous matrixes etc. The solid phase is preferably synthetic microparticles preferably made of polystyrene, vinyl chloride or latex of 0.1 to 10 microns in diameter.

II. METHODS FOR FRACTIONATING POLYCLONAL ANTIBODIES TO ANALYTES

The present invention also presents methods for fractionating polyclonal antibodies to Analytes to yield fractions containing HE Antibodies and Non-HE Antibodies, respectively. Polyclonal antibodies to Analytes can be produced using methods known in the art. For example, the antibodies can be produced by injecting a host animal such as a rabbit, rat, goat, mouse, etc., with the Analyte or fragments thereof, alone or conjugated to an appropriate carrier, if required, to elicit an antibody response.

This method comprises exposing the polyclonal antibodies to a Analyte which has its HE site masked ("masked Analyte") by either a Binding Molecule or an HE Antibody. The antibodies that bind the masked Analyte, and which can be eluted, are Non-HE Antibodies which bind both free Analyte and the complex of Analyte-Binding Molecule. Thus, immunoassays using Non-HE Antibodies to detect the Analyte, which may be present in free or complexed, forms, will not exhibit a bias. The Non-HE Antibodies thus obtained can be used in both MOLY (as either probe or capture antibodies, or both) and competitve (as capture antibodies) immunoassays. On the other hand, the polyclonal antibodies that do not bind the masked Analyte are HE Antibodies. HE Antibodies could be used in assays specific for free Analyte or as described above for addition in Analyte assays (whether MOLY or MONO immunoassays) suffering from a bias to alleviate or eliminate such bias.

The above fractionation is preferably conducted using affinity chromatography. Preferably, the masked Analyte is cross-linked to the Binding Molecule, HE Antibodies, or Non-HE Antibodies. The cross-linking can be achieved by methods known in the art or modification of such which is within the knowledge of one skilled in the art. Examples of publications which disclose methods for cross-linking molecules are: Ji, T. H., *Methods in Enzymology*, 91:580 (1983); Wong, S. S., et al., in Chapter 22, 266–282 of *Biocatalyst Design for Stability and Specificity*. Eds. M. E. Himmel and G. Georgiou, American Chemical Society, Washington, DC (1993); M. N. Gupta in Chapter 26, 307–326 of *Biocatalyst Design for Stability and Specificity*, Eds. M. E. Himmel and G. Georgiou, supra; *Chemical Reagents for Protein Modification.* 2nd ed., R. L. Lundblad, CRC Press, Boston. These publications are herein incorporated by reference.

Preferably, the resulting complex is bound to a solid, directly or by means of a binding agent such as a HE Antibody which is immobilized on the solid phase, and used in affinity chromatography to select for the HE Antibodies. The general methods for affinity chromatograpy, such as the preparations of the antibodies and solid phase, and the procedures are known in the art, see e.g. Bio-Rad Bulletin 1099, *Immunoaffinity Chromatography with Affinity Supports* (1990); Pharmacia LKB Biotechnology, *Affinity Chromatography, Principles & Methods* (1993); and *Methods in Molecular Biology*, vol. 10, "Immunochemical Protocols", ed. M. M. Manson, p. 89–91 (1992); *Immunochemistry in Practice*, A. Johnstone, et al., Chapter 10, 202–232, Scientific Publications, Oxford (1982); and *Current Opinion in Biotechnology*, vol. 2, "Affinity Chromatography for Protein Isolation", W. H. Scouten, 37–43 (1991). These publications are herein incorporated by reference.

Figure 3A:
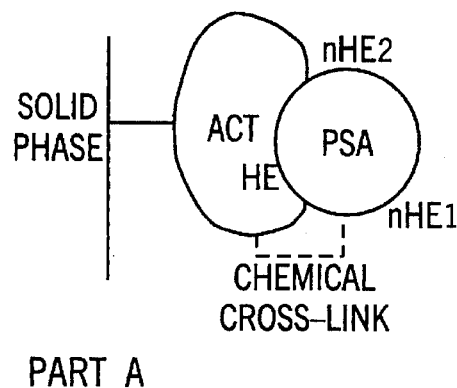
FIG. 3A is an illustration of a Part A in a method for obtaining polyclonal antibodies to hidden and non-hidden epitopes on PSA.
Figure 3B:
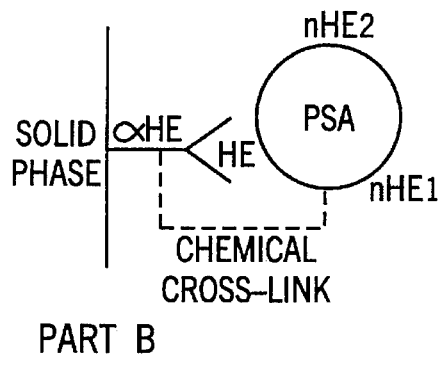
FIG. 3B is an illustration of a Part B in a method for obtaining polyclonal antibodies to hidden and non-hidden epitopes on PSA.
Figure 3C:
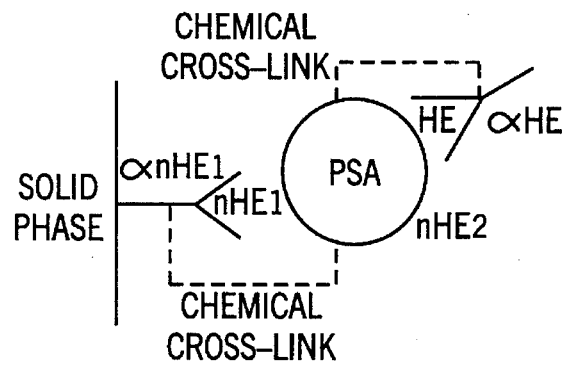
FIG. 3C is an illustration of a Part C in a method for obtaining polyclonal antibodies to hidden and non-hidden epitopes on PSA.

FIG. 3A, 3B and 3C illustrates the three methods for fractionating polyclonal antibodies into HE Antibodies and Non-HE Antibodies using PSA, ACT and $HE_{PSA}$ Antibodies as examples. The methods are as follow:

Part A

Use of ACT to bid PSA Use of ACT to Bind PSA.

ACT is conjugated to a solid phase, such as cyanogen bromide-activated Sepharose-4B (commercially available from Pharmacia LKB Biotechnology, Sweden). Purified PSA is allowed to react with the ACT to form a PSA-ACT complex that masks the hidden epitopes (HE). The complex can be further stabilized by chemical cross-linking. When polyclonal antibodies to PSA are incubated with the PSA-ACT-solid phase, $HE_{PSA}$ Antibodies will be unbound. Non-$HE_{PSA}$ Antibodies specific for non-hidden epitopes, such as nHE1 and nHE2, will be bound and can be eluted with standard methods, such as low pH. Thus, the polyclonal anti-PSA antibodies are separated into $HE_{PSA}$ and Non-$HE_{PSA}$ Antibodies.

Part B

Use of Antibodies to Hidden Epitopes (αHE) to Bind PSA
Use of $HE_{PSA}$ Antibodies (αHE) to Bind PSA $HE_{PSA}$ Antibodies (αHE) are conjugated to a solid phase, such as cyanogen bromide-activated Sepharose-4B. Purified PSA is allowed to react with the αHE to form a PSA-αHE complex that masks the hidden epitopes (HE). The complex can be further stabilized by chemical cross-linking. When polyclonal antibodies to PSA are incubated with the PSA-αHE solid phase, polyclonal $HE_{PSA}$ Antibodies will not be bound to the solid phase. On the other hand, polyclonal Non-$HE_{PSA}$ Antibodies will be bound and can be eluted with standard methods, such as low pH. It shall be noted that if a particular αHE does not mask all the HE on the PSA, then additional HE Antibodies directed to other HE sites can be used simultaneously or preferably, in sequential fractionation columns.

Part C

Use of Antibody to Non-Hidden Epitope (αHE1) to Bind PSA Followed by use of Antibody to Hidden Epitopes (αHE) to Block HE Use of Non-HE$_{PSA}$ Antibodies (αHE1) to Bind PSA Followed by Use of HE$_{PSA}$ Antibody (αHE) to Block HE Non-HE$_{PSA}$ Antibodies (αnHE1) directed to non-hidden epitope 1 (nHE1) are conjugated to a solid phase, such as cyanogen bromide-activated Sepharose-4B. Purified PSA is allowed to react with the αnHE1 to form a PSA-αnHE1 complex. An HE$_{PSA}$ Antibody (αHE) is allowed to react with the PSA-αnHE1 to form a complex that masks the hidden epitopes (HE). The complex can be further stabilized by chemical cross-linking. When polyclonal antibodies to PSA are incubated with the solid phase-αnHE1-PSA-αHE, antibodies to HE and HE1 will not bind to the solid phase. Non-HE$_{PSA}$ Antibodies to non-hidden epitopes other than nHE1 will be bound to the solid phase and can be eluted with standard methods, such as low pH. The antibodies that do not bind to the solid phase can be further separated by methods A or B. Thus, the polyclonal anti-PSA antibodies are separated into HE$_{PSA}$ Antibodies, Antibodies to nHE1 and nHE other than nHE1. It shall be noted that if a particular αHE does not mask all the HE on the PSA, then additional HE Antibodies directed to other HE sites can be used simultaneously or in sequential fractionation columns.

III. COMPLEXES OF ANALYTE-HE ANTIBODIES USEFUL AS CALIBRATORS AND CONTROLS FOR PSA ASSAYS

Another aspect of the invention presents a complex of Analyte-HE Antibody which can serve as a calibrator and control in an assay for Analytes. The complex can be formed by adding an excess of HE Antibodies to the Analyte. The HE Antibodies are preferably at a 2-fold to 100-fold, and a more preferred 10-fold excess to the Analyte. Alternatively, the Analyte can be cross-linked to the HE Antibodies. The method described above for cross-linking Analyte and Binding Molecule are similarly applicable for cross-linking Analyte and HE Antibodies. The complex is preferably stored in an inert buffer such as phosphate buffered saline, Tris-HCl, or HEPES. The storage temperature preferably ranges from 2° C. to 25° C. The pH is preferably between 5 to 9. A cross-linked complex of the Analyte and its Binding Molecule useful as a calibrator or control in an assay for the Analyte can also be similarly produced.

The following examples illustrate the present invention and are not to be construed as limiting it.

EXAMPLES

Example I

New PSA Assay Method

The following experiment was conducted using the reagents for IMx® PSA Assay and conducted on the IMx® instrument (Abbott Laboratories, Abbott Park, Ill.) following the protocol in the IMx® PSA Assay's accompanying package insert, except that in this invention, the Assay Diluent additionally contained 0 to 20 ug/mL of MAB 9B10 or 5A10 (discussed above) which bind free PSA but not PSA-ACT complex. The IMx® PSA Assay reagents include the following: (1) microparticles coated with capture antibody MAB H50 ("Anti-PSA Coated Microparticles") which bind and capture both free and complexed PSA (i.e. PSA complexed to ACT) onto the microparticles; and (2) goat polyclonal antibodies to PSA (which serve as probe antibodies) which are labelled with alkaline phosphatase for detection ("goat polyclonal Anti-PSA: Alkaline Phosphatase Conjugate" or "probe polyclonal antibodies").

The samples tested were pooled serum samples from patients with prostate cancer.

The descriptions of the IMx® instrument, its operation and general protocol can be found in Barnes et al., *J. Clin. Imm.*, 14 (2): 115–119 (1991) and EP-A-288,793; Ludington et al., *Clin. Chem.*, 34(9), 1726–1732 (1988)). The components of the reaction cells are shown in FIG. 2(a) of *Clin. Chem,*, 34: (9), at 1727. In this case, the reaction scheme is that of a microparticle enzyme immunoassay (MEIA), as follows:

(1) The probe/elect, rode assembly of the IMx® instrument delivers the sample, Anti-PSA Coated Microparticles and Assay Diluent to the incubation well of the reaction cell. During the incubation of this reaction mixture, the free and complexed PSA in the sample bind to the Anti-PSA Coated Microparticles forming an antibody-antigen complex. MAB 9B10 in turn binds the PSA (which is not complexed to ACT) that is bound to the Anti-PSA Coated Microparticles, to form an antibody-antigen-antibody complex.

(2) An aliquot of the reaction mixture is transferred to the glass fiber matrix of the IMx® instrument. The microparticles bind irreversibly to the glass fiber matrix.

(3) The matrix is washed to remove unbound materials, e.g. serum proteins, Assay Diluent, and MAB 9B10 that are not bound to the microparticles.

(4) The goat polyclonal Anti-PSA: Alkaline Phosphatase Conjugate is dispensed onto the matrix and binds to the antibody-antigen-antibody complex.

(5) The matrix is washed to remove unbound materials.

(6) The substrate, 4-methylumbelliferyl phosphate (MUP), is added to the matrix and the surface-bound alkaline phosphatase converts the nonfluorogenic MUP to 4-methylumbelliferone (MU), whose fluorescence is measured by the MEIA optical assembly of the IMx® instrument.

The above assay steps were run separately but concurrently using calibrators and controls containing free PSA, instead of samples. The readings for the samples (i.e. panels) were read off the calibrators (of Table 1 below) to arrive at the PSA values reported in Tables 2 and 3 below.

TABLE 1

| Calibrators (Free PSA) | MAB 9B10 Concentration in Assay Diluent (ug/ml) | | | |
|---|---|---|---|---|
| (ng/ml) | 0 | 5 | 10 | 20 |
| 0 | 7.0 | 6.3 | 6.4 | 6.1 |
| 2 | 90.9 | 58.0 | 58.3 | 57.4 |
| 10 | 373.6 | 248.6 | 248.8 | 247.1 |
| 30 | 877.3 | 640.1 | 623.4 | 606.3 |
| 60 | 1394.8 | 1084.8 | 1084.8 | 1053.7 |
| 100 | 1834.3 | 1486.1 | 1520.8 | 1493.8 |

The readings were taken in c/s/s.

TABLE 2

| Controls | MAB 9B10 Concentration in Assay Diluent (ug/ml) | | | |
|---|---|---|---|---|
| (Free PSA) | 0 | 5 | 10 | 20 |
| Low (3–5 ng/ml) | 3.98 | 4.14 | 4.17 | 3.86 |
| Medium (12–18 ng/ml) | 15.18 | 15.02 | 15.12 | 14.95 |
| High (36–54 ng/ml) | 46.90 | 42.85 | 45.87 | 48.20 |

The readings are reported in ng/ml.

TABLE 3

| Panels (Pooled Prostate Cancer Patient Sera) | MAB 9B10 Concentration in Assay Diluent (ug/ml) | | | |
|---|---|---|---|---|
|  | 0 | 5 | 10 | 20 |
| JP1 | 50.49 | 77.88 | 83.71 | 85.72 |
| C8 | 1.37 | 2.01 | 2.02 | 2.08 |
| C9 | 3.25 | 5.06 | 4.97 | 5.16 |
| C10 | 13.02 | 18.99 | 19.21 | 19.69 |
| C11 | 36.65 | 60.88 | 62.62 | 64.93 |
| 92-297-0384 | 26.59 | 48.15 | 47.71 | 50.13 |

The readings are reported in ng/ml.

The above Tables show that increasing amounts of free MAB 9B10 in the assay reduced the calibration curve signals and increased sample panel values.

The effect of MAB 9B10 on panel values appears to plateau at about 10 ug/ml. The above experiments were repeated using MAB 5A10 in place of MAB 9B10 and the results were similar.

In the following experiment, the above plateau level of 10 ug/ml of MAB 9B10 in Assay Diluent was used to demonstrate bias between free and complexed PSA. A sample containing free PSA was mixed with purified ACT and allowed to form complexes. Purified PSA and ACT were obtained from Dr. Hans Lilja, University of Malmo. Purification of PSA and ACT and formation of complexes of PSA and ACT have been previously described (A. Christensson, et al., *Eur. J. Biochem.* 194: 755–763, 1990). Purified seminal fluid PSA in 0.1 M phosphate buffer, pH 7.0 containing 7.5% bovine serum albumin and 0.05% sodium azide was mixed with a 100 molar excess of purified ACT. A control sample of PSA was mixed with buffer instead of ACT. These samples were allowed to incubate overnight at 35° C.

Following the incubation, these samples were assayed in the IMx® PSA assay with the following modifications:

a. Abbott IMx® PSA Assay (no modifications)
b. Abbott IMx® PSA Assay with 9B10 in Assay Diluent (i.e. with the addition of 10 ug/mL of 9B10 to the Assay Diluent)
c. Abbott IMx® PSA Assay with MAB H50 probe and MAB H117 capture antibodies (i.e. with the use of H117 coated microparticles and labelled H50)

The assay was performed as described above. Table 4 shows the amounts of PSA obtained for the free PSA samples and for the PSA samples which had ACT added. Bias is indicated by the reduction of the amount of PSA detected in the sample containing ACT as compared to the PSA control.

TABLE 4

| Assay Tested | Free PSA | PSA + ACT | % Bias |
|---|---|---|---|
| Abbott IMx® PSA Assay | 64.7 | 40.9 | 36.8 |
| Abbott IMx® PSA Assay with 9B10 in Assay Diluent | 67.2 | 61.3 | 8.8 |
| Abbott IMx® PSA Assay with MAB H50 probe antibodies and MAB H117 capture antibodies | 68.8 | 70.1 | −1.8 |

The readings were taken in ng/ml

The data in Table 4 shows that the MONO assay (with MAB H50 as probe antibodies and MABH 117 as capture antibodies) has no bias. In contrast, the MOLY assay (Abbott IMx® PSA Assay) has a 36.8% bias which is dramatically reduced by the addition of free MAB 9B10 to the assay.

The above experiment was repeated, wherein the MONO assay used MAB H50 as capture antibody and MAB H117 as probe antibody. It was observed that such a MONO assay also suffered from bias which can be eliminated by the addition of free 9B10 in the Assay Diluent.

Example II

PSA-HE Antibody Complex Useful As Calibrators and Controls

The mixture of $HE_{PSA}$ Antibodies with PSA results in the formation of a PSA-$HE_{PSA}$ Antibodies complex in which the hidden epitopes are blocked similarly to PSA-ACT complex. This material can be used as a calibrator or control in PSA assays.

Seminal fluid PSA in 0.01 M phosphate buffered saline, pH 7.4 is mixed with 9B10 at a 10-fold excess and incubated overnight at 2–8 degrees C. Following incubation, the PSA-$HE_{PSA}$ Antibody complex is diluted in IMx® PSA Calibrator Diluent at levels of 0, 2, 10, 30, 60 and 100 ng/mL. These calibrators can be used in the IMx® PSA assay and mimic PSA-ACT complexes by masking the HE on PSA.

Example III

Cross-Linking HE Antibody to Free PSA for Selecting Polyclonal Antibodies to PSA HE and PSA non-HE This example describes the implementation of the fractionation method shown in Part B of FIG. 2 discussed above. MAB 5A10 is used to illustrate the method though any $HE_{PSA}$ Antibody can be used in its place, such as MAB 9B10.

In the initial step, 5A10 is cross-linked to cyanogen bromide-activated Sepharose-4B based on manufacturer's recommendations. (*Affinity Chromatography Principles and Methods*, Pharmacia LKB Biotechnology, Sweden, 23–30 (1993)).

The procedure is as follows:

The 5A10 for Affinity Column is mixed with 0.1 M sodium phosphate dibasic ($Na_2HPO_4$) and the pH is adjusted to 9.0. 5A10 is then mixed with cyanogen bromide-activated Sepharose-4B gel at a ratio of 2 mg 5A10 per mL of gel. The mixture is incubated at 2°–8° C. overnight with gentle shaking.

Following the coupling of 5A10 to the Sepharose gel, the gel is washed with 0.1M $Na_2HPO_4$, pH 8.0, to remove any unbound ligand, and then mixed with 1M ethanolamine, pH 8.0, at 2°–8° C. to block any active groups remaining in the gel. The gel is washed with distilled or deionized water followed by two alternating cycles of 0.1M sodium acetate buffer with 1 M NaCl pH 4.0 and 0.1M $Na_2HPO_4$ with 1M NaCl, pH 8.0. A column is poured, washed with PBS solution (0.01M $NaHPO_4$, 0.15M NaCl, pH 7.2) and then eluted with 0.1M glycine, 0.1M NaCl, pH 2.5. The column is then washed with PBS at pH 7.2 containing 0.1% sodium azide. The 5A10 affinity column is stored at 2°–8° C.

The next step in the procedure involves the binding of PSA to the Sepharose 4B-5A10 followed by chemical crosslinking to stabilize the 5A10-PSA complex. Binding of PSA to 5A10 blocks the HE on the PSA so that the HE cannot bind other $HE_{PSA}$ antibodies. The procedure for cross-linking insoluble proteins with the cross-linking agent, dimethylpalemidate (DMP) has previously been described. (C. Schneider, et al., *J. Biol. Chem.* 25, 10766–10769, (1982)).

The next procedure is as follows:

Remove the Sepharose 4B-5A10 gel from the column and place it in a graduated cylinder. After the gel has settled, remove the residual buffer. For each mL of packed gel, add 10 mg of purified PSA at an initial concentration of 2 mg/mL in 0.01M phosphate buffer, pH 7.4. Transfer to an Erlenmeyer flask and incubate at 2°–8° C. overnight with gentle shaking.

Following overnight incubation, wash the gel twice in 10 volumes of 0.2M triethanolamine, pH 9.0 (TEA) on a Buchner funnel. Transfer the gel to a beaker and add 5 parts of 40 mM DMP in TEA, pH 9.0. Incubate with shaking for 1 hour at room temperature. Using a Buchner funnel wash with 10–20 volumes of TEA, pH 9.0 and 10–20 volumes of 0.01M phosphate buffered saline, pH 7.4 with 0.02% sodium azide. Transfer gel to column.

The final step of the process is to purify polyclonal antibodies to PSA over the Sepharose 4B-5A10-PSA column by standard affinity procedures as follows:

Dilute the anti-PSA polyclonal antibodies 1:1 with column buffer (0.01M phosphate buffered saline, pH 7.4). (Examples of polyclonal antibodies are goat, rabbit, sheep, mouse, and rat polyclonal antibodies.) Slowly, load the sample onto the column. Collect the protein that does not bind to the column. This fraction contains the HE antibodies. Wash the column with column buffer and monitor the OD at 280 nm. When the absorbance falls to baseline, rapidly elute the bound non-HE Antibodies with 0.1M glycine-HCl, pH 2.5. Collect fractions into an equal volume of 0.1M Tris-HCl, pH 8.5 to rapidly adjust the pH to neutrality. Both the purified HE and non-HE antibodies may be dialyzed into the desired buffer and stored at 2°–8° C. following filtration through a 0.2 micron sterile filter. Alternatively, the antibodies may be frozen.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allow for obvious changes in the basic invention herein are also within the claims.

We claim:

1. An immunoassay method for detecting or quantitating an Analyte ("A") in a sample, the Analyte being capable of existing in the sample in a free form ("free Analyte") or bound to a Binding Molecule to form a complex of the Analyte and the Binding Molecule ("{(A)(Binding Molecule)}"), the method comprising the steps of:

(a) contacting the Analyte to an antibody ("αHE") which can bind the free Analyte but not {(A)(Binding Molecule)}, a capture antibody ("αnHE") which can bind both the free Analyte and {(A)(Binding Molecule)}, and a probe antibody ("αA*") specific for the Analyte, providing that if the probe antibody is a polyclonal antibody then the Analyte is contacted to the capture antibody before the probe antibody;

(b) correlating the presence or amount of αA* which is bound to the Analyte, with the presence or amount of the Analyte in the sample, or correlating the amount of unbound αA* with the absence or amount of the Analyte in the sample.

2. The immunoassay method of claim 1, wherein the sample is a biological sample.

3. The immunoassay method of claim 2, wherein the Analyte and Binding Molecule are endogenous to the biological sample.

4. The immunoassay method of claim 3, wherein the Analyte and Binding Molecule are proteins.

5. The immunoassay method of claim 1, wherein the probe antibody is a polyclonal antibody.

6. The immunoassay method of claim 5, wherein the capture antibody is a monoclonal antibody.

7. The immunoassay method of claim 6, wherein the capture antibody is bound to a solid phase.

8. The immunoassay method of claim 7, further comprising the step of separating the sample and unbound αHE from the solid phase, before adding αA* to the solid phase, and then separating the unbound αA* and detecting the αA* bound to the solid phase.

9. The immunoassay method of claim 6, wherein the probe antibody is a population of polyclonal antibodies comprising antibodies which bind the free Analyte and not {(A)(Binding Molecule)}, and antibodies which bind both the free Analyte and {(A)(Binding Molecule)}.

10. The immunoassay method of claim 1, wherein αHE is a MAB.

11. The immunoassay method of claim 1, wherein the probe antibody is labelled for detection.

12. The immunoassay method of claim 11, wherein the probe antibody is labelled with a chemiluminiscent, enzymatic, radioactive, or fluorescent label.

13. The immunoassay method of claim 1, wherein the Analyte is a serum protease and the Binding Molecule is a serum protease inhibitor.

14. The immunoassay method of claim 1, wherein the Analyte and its corresponding Binding Molecule (in parenthesis) are selected from the group consisting of: protein C (protein C inhibitor); elastase (anti-trypsin); cathepsin G (ACT); PSA (ACT); PSA ($\alpha_2$-macroglobulin); thrombin (anti-thrombin III); $C_1$-esterase ($C_1$-inhibitor); t-PA (PAI-1); uPA (PAI-1); plasmin ($\alpha_2$-antiplasmin); PSA ($\alpha_1$-protease inhibitor); and PSA (protein C inhibitor), and vice versa.

15. The immunoassay method of claim 14, wherein the Analyte is PSA and the Binding Molecule is ACT.

16. The immunoassay method of claim 15, wherein the probe antibody is a polyclonal antibody.

17. The immunoassay method of claim 16, wherein the capture antibody is a monoclonal antibody.

18. The immunoassay method of claim 17, wherein αHE is a MAB.

19. The immunoassay method of claim 18, wherein the capture antibody is bound to a solid phase.

20. The immunoassay method of claim 18, wherein the αHE is selected from the group of MAB consisting of:

9B10, 5A10, PSA6, PSA30, PSA17, PSA19, PSA20, and PSA25.

21. The immunoassay method of claim 1, wherein the capture antibody and probe antibody are MAB.

22. The immunoassay method of claim 21, wherein αHE is a MAB.

23. A kit for conducting an assay for Analyte in a sample, wherein the Analyte can exist in the sample as a free Analyte or bound to a Binding Molecule to form a complex of Analyte-Binding Molecule Complex, the kit comprising the following:

(a) a first container containing an antibody (αHE) specific to the Analyte which can bind to the free Analyte but not Analyte-Binding Molecule Complex;

(b) a second container containing a capture antibody specific for the Analyte; and (c) a third container containing a probe antibody specific for the Analyte.

24. The kit of claim 23, wherein the capture antibody is bound to a solid phase.

25. The kit of claim 23, further comprising a container containing a complex of Analyte bound to αHE.

26. The kit of claim 23, wherein the probe antibody is labelled for detection, and the kit further comprises a fourth container containing a reagent which reacts with the label on the probe antibody to produce a detectable signal.

27. The kit of claim 26, wherein the capture antibody is bound to a solid phase.

28. The kit of claim 27, wherein the Analyte is PSA, the Binding Molecule is ACT, the capture antibody and αHE are MAB, and the probe antibody is a polyclonal antibody.

29. The kit of claim 27, wherein the Analyte is PSA, the Binding Molecule is ACT, the capture antibody, probe antibody and αHE are MAB.

30. A kit for conducting an assay for Analyte in a sample, wherein the Analyte can exist in the sample as a free Analyte or bound to a Binding Molecule to form a complex of Analyte-Binding Molecule Complex, the kit comprising the following:

(a) a first container containing:
 (i) a capture antibody specific for the Analyte, and
 (ii) an antibody (αHE) specific to the Analyte which can bind the free Analyte but not the Analyte-Binding Molecule Complex; and (b) a second container containing a probe antibody specific for the Analyte.

31. A kit for conducting an assay for Analyte in a sample, wherein the Analyte can exist in the sample as a free Analyte or bound to a Binding Molecule to form a complex of Analyte-Binding Molecule Complex, the kit comprising the following:

(a) a first container containing a capture antibody specific for the Analyte; and (b) a second container containing:
 (i) an antibody (αHE) specific to the Analyte which can bind the free Analyte but not the Analyte-Binding Molecule Complex, and
 (ii) a probe antibody specific for the Analyte.

32. An immunoassay method for detecting or quantitating an Analyte ("A") in a sample, the Analyte being capable of existing in the sample in a free form ("free Analyte") or bound to a Binding Molecule to form a complex of {(A)(Binding Molecule)}, the method comprising the steps of:

(a) incubating the sample with polyclonal capture antibodies ("αA") which contain antibodies which bind the free Analyte and antibodies which bind {(A)(Binding Molecule)};

(b) incubating the sample with an antibody αHE capable of binding free analyte but not {(A) (Binding Molecule)} for a sufficient time for the αHE to bind to the Analyte;

(c) incubating the sample with a probe antibody ("αnHE*") capable of binding both the free Analyte and {(A)(Binding Molecule)}; and (d) correlating the presence or amount of αnHE* bound to the Analyte with the presence or amount of Analyte in the sample; or correlating the amount of unbound αnHE* with the absence or amount of the Analyte in the sample.

33. An immunoassay method for defecting or quantitating Analyte ("A") in a sample, the Analyte being capable of existing in the sample in a free form ("free Analyte") or bound to a Binding Molecule to form a complex of {(A)(Binding Molecule)}, the method comprising the steps of:

(a) incubating the sample with a capture antibody ("αnHE") which can bind both free Analyte and {(A)(Binding Molecule)}, for a sufficient time for the capture antibody to bind to any Analyte and {(A)(Binding Molecule)} that may be present in the sample to form complexes of {(αnHE)(A)} and {(αnHE)(A)(Binding Molecule)}, respectively;

(b) incubating the sample with an antibody αHE which can bind the free Analyte but not {(A) (Binding Molecule)} for a sufficient time for the αHE to bind to the Analyte;

(c) incubating the sample with a probe antibody ("αA*") specific for the Analyte for a sufficient time to bind to the Analyte;

(d) detecting the presence or amounts of the complexes of {(αnHE)(A)(αHE)(αA*)} and {(αnHE)(A)(Binding Molecule)(αA*)}, or free αA*; and (e) correlating the presence or amounts of {(αnHE)(A)(αHE)(αA*)} and {(αnHE)(A)(Binding Molecule)(αA*)} with the presence or amount of the Analyte in the sample; or correlating the amount of free αA* with the absence or amount of the Analyte in the sample.

* * * * *